United States Patent [19]

Staniland

[11] 4,453,010

[45] Jun. 5, 1984

[54] PRODUCTION OF HYDROXY ARYLOPHENONES

[75] Inventor: Philip A. Staniland, Tewin Wood, England

[73] Assignee: Imperial Chemical Industries PLC, London, England

[21] Appl. No.: 341,182

[22] Filed: Jan. 20, 1982

[30] Foreign Application Priority Data

Feb. 4, 1981 [GB] United Kingdom ............... 8103438

[51] Int. Cl.$^3$ ............................................. C07C 45/46
[52] U.S. Cl. .................................... 568/319; 568/322; 568/306
[58] Field of Search ...................... 568/319, 322, 306

[56] References Cited

U.S. PATENT DOCUMENTS

| 2,483,566 | 10/1949 | Thompson | 568/319 |
| 3,073,866 | 1/1963 | Stanley | 568/319 |

FOREIGN PATENT DOCUMENTS

| 1066542 | 4/1967 | United Kingdom | 568/379 |
| 1164046 | 9/1969 | United Kingdom | 568/319 |
| 1344864 | 1/1974 | United Kingdom | 560/255 |

OTHER PUBLICATIONS

Hocking, J. Chem. Tech. Biotechnol., vol. 30, pp. 626-641 (1980).
Effenberger et al., Angew. Chemie. Int. Edit., vol. 12, pp. 775-776 (1973).
Premasoger et al., J. Org. Chem., vol. 46, pp. 2974-2976 (1981).

*Primary Examiner*—James H. Reamer
*Attorney, Agent, or Firm*—Cushman, Darby & Cushman

[57] ABSTRACT

Production of a hydroxy arylophenone by reacting an aromatic carboxylic acid Ar(—CO$_2$H)$_p$ where Ar is an aromatic radical, (—CO$_2$H) is an aromatic carboxylic acid group, and p is 1 or 2 with an aromatic compound H—Ar'—OH where Ar' is an aromatic radical and —H and —OH are aromatically bound para to each other in a benzenoid ring, in the presence of an alkyl sulphonic acid, particularly methane sulphonic acid, to produce a hydroxy arylophenone of formula Ar(—CO—Ar'—OH)$_p$ where the carbonyl and hydroxyl groups are para to each other in the hydroxyl-containing benzenoid ring of Ar'. The production of the hydroxy arylophenone proceeds through the intermediate ester (H—Ar'—O—CO—)$_p$Ar and the production of the hydroxy arylophenone starting from the ester is also claimed.

15 Claims, No Drawings

PRODUCTION OF HYDROXY ARYLOPHENONES

The present invention relates to processes for the production of hydroxy arylophenones.

Hydroxy arylophenones are commercially useful substances and have been employed, for example, in the preparation of dyestuffs, polymers and ultraviolet absorption agents.

Conventional prior art processes for making hydroxy arylophenones include aromatic acylation using an aromatic acid chloride and a Friedels-Craft catalyst such as $AlCl_3$, or an aromatic ester Fries rearrangement, also using a metallic halide catalyst such as $AlCl_3$, the ester having been formed from a phenol and an aromatic acid chloride.

It is also known to prepare hydroxy arylophenones by aromatic acylation using an aromatic carboxylic acid, with liquid HF being employed as a condensing agent; such a process is described in British Pat. No. 1,164,046.

The HF catalysed reactions are advantageous in that the carboxylic acids employed therein are usually cheaper and more readily available than the corresponding acid halides, and in that there are no metallic catalyst residues which might contaminate the resulting arylophenone. Nevertheless, the use of liquid HF is best avoided where possible because of its extremely corrosive properties and physiologically harmful action and the necessity of using pressure equipment.

It is also known from U.S. Pat. No. 3,073,866 to prepare hydroxy arylophenones by condensing an aromatic carboxylic acid with a phenol in the presence of $ZnCl_2$, $PCl_3$ and polyphosphoric acid. While the patent specifies that the hydroxy arylophenones are produced in good yield and high purity using this process, I have found that the product is in fact highly coloured and difficult to obtain in a pure state in high yield. The reaction also poses effluent problems in that the contaminated phosphoric acid residue cannot be recovered economically but must be disposed of. Additionally, the presence of a metallic halide catalyst is undesirable for the reason given above.

I have now discovered a process for making hydroxy arylophenones using an aromatic carboxylic acid which does not require the use of liquid HF or the $ZnCl_2$/$PCl_3$/polyphosphoric acid system as the condensing agent.

According to the present invention there is provided a process for the production of a hydroxy arylophenone which comprises reacting an aromatic carboxylic acid of formula $Ar(-CO_2H)_p$ where Ar is an aromatic radical, ($-CO_2H$) is an aromatically bound carboxylic acid group, and p is an integer of 1 or 2, with an aromatic compound of formula H—Ar'—OH where Ar' is an aromatic radical containing at least one benzenoid ring and the hydrogen atom —H and hydroxyl group —OH are aromatically bound para to each other in a benzenoid ring, in the presence of an alkane sulphonic acid to produce a hydroxy arylophenone of formula Ar-$(-CO-Ar'-OH)_p$ where the carbonyl group is para to the hydroxyl group in said hydroxyl-containing benzenoid ring of Ar'.

Thus the process of the invention employs an alkane sulphonic acid as the condensing agent instead of liquid HF or the $ZnCl_2$/$PCl_3$/polyphosphoric acid system. These materials are (or if solid are converted on melting into) high boiling liquids and do not require the use of pressure equipment. While being corrosive, they are far easier and safer to handle than liquid HF. They also do not incur the use of a metallic halide and so are advantageous in this respect as well.

Examples of alkane sulphonic acids which may be used include methane sulphonic acid, ethane sulphonic acid, propane sulphonic acid, C4–C20 alkane sulphonic acids, and benzyl sulphonic acid; it is thus apparent that the term alkane includes aralkane. It is to be understood that, apart from possible aryl substituents the alkyl hydrogen atoms of the alkane sulphonic acids are unsubstituted. Of the alkane sulphonic acids, methane sulphonic acid is particularly preferred and enables the hydroxy arylophenone to be prepared in good yield and high purity (if this is required); it is also an excellent solvent for the starting materials and products which also facilitates the effectiveness of the process.

The aromatic radical Ar of the aromatic carboxylic acid may be nuclear unsubstituted (apart from the carboxylic acid group or groups) or have one or more nuclear substituents provided that the substituent(s) does not deleteriously affect the condensation reaction. Preferably, the aromatic carboxylic acid contains only one carboxylic group, i.e. p is 1 and preferred aromatic carboxylic acids that may be used have the formula

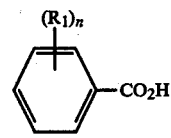

where n is 0, 1, 2, 3, 4, or 5; and $R_1$ which may be the same or (where $n \geq 2$) different represents alkyl or substituted alkyl (preferably of 1 to 18 carbon atoms, more preferably of 1 to 5 carbon atoms), alkoxy or substituted alkoxy (preferably of 1 to 18 carbon atoms, more preferably of 1 to 5 carbon atoms), hydroxyl, halogen (preferably F or Cl), nitro, amino, aryl including nuclear substituted aryl (preferably phenyl), or (when n=1) an aromatic ring (preferably a benzenoid ring) fused to the benzene ring. Preferably n is 0, 1, 2, or 3, and $R_1$ is hydroxyl, alkyl (1 to 5 carbon atoms) alkoxy (1 to 5 carbon atoms), F, Cl, or (when n=1) a benzenoid ring fused to the benzene ring.

Illustrative examples of aromatic carboxylic acids which may be used in the process of the invention are benzoic acid (i.e. n=0); salicylic acid; 3-methyl salicylic acid; 3-hydroxy benzoic acid; 4-hydroxy benzoic acid; 4-chloro benzoic acid; 3-chloro benzoic acid; 2-chloro benzoic acid; 4-fluoro benzoic acid; 3-fluoro benzoic acid; 2-fluoro benzoic acid; 2-methoxy benzoic acid; 2-ethoxy benzoic acid; 3-methoxy benzoic acid; 3-ethoxy benzoic acid; 2,3-dihydroxy benzoic acid; 2,4-dihydroxy benzoic acid; 2,3,4-trihydroxy benzoic acid; 2-hydroxy-4-methoxy benzoic acid; 2-methoxy-4-hydroxy benzoic acid; 2-hydroxy-3-methoxy benzoic acid; 2,4 and 2,5-dimethyl benzoic acids; 4-methoxy benzoic acid; O-, m- and p-toluic acids; 4-hydroxy-3,5-di-C1 to C5 alkyl benzoic acids such as 4-hydroxy-3,5-dimethyl benzoic acid; 4-phenyl-benzoic acid; 1 and 2-naphthoic acids; 1-hydroxy-2-naphthoic acid; 3-hydroxy-2-naphthoic acid; terephthalic acid; and isophthalic acid.

The aromatic radical Ar' of the compound H—Ar'—OH may be nuclear unsubstituted (apart from the hydroxyl group) or have one or more nuclear substituents provided that the substituent(s) does not deleteriously affect the condensation reaction. Preferred aromatic compounds H—Ar'—OH have the formula:

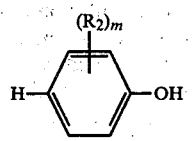

where m is 0, 1, 2, 3 or 4; $R_2$ which may be the same or (where $m \geq 2$) different represents alkyl or substituted alkyl (preferably of 1 to 18 carbon atoms, more preferably of 1 to 5 carbon atoms), alkoxy or substituted alkoxy (preferably of 1 to 18 carbon atoms, more preferably of 1 to 5 carbon atoms), hydroxyl, halogen (preferably F or Cl), nitro, amino, aryl including nuclear substituted aryl (preferably phenyl), or (when m=1) an aromatic ring (preferably a benzenoid ring) fused to the benzene ring. Preferably m is 0, 1, or 2, and $R_2$ is alkyl (1 to 5 carbon atoms), alkoxyl (1 to 5 carbon atoms), F, Cl, hydroxyl, or (when m=1) a benzenoid ring fused to the benzene ring.

Illustrative examples of aromatic compounds H—Ar'—OH which may be used in the present invention are phenol (i.e. m=0); o- and m-cresols; catechol; resorcinol; o-chloro phenol; m-chloro phenol; 3,5-xylenol; o-methoxy phenol; o-propoxy phenol; m-methoxy phenol; m-ethoxy phenol; and 1-naphthol.

Illustrative of hydroxy arylophenones prepared by the above-defined process of the invention are:

4,4'-dihydroxy-benzophenone; 4-hydroxy-benzophenone; 4-hydroxy-4'-chloro-benzophenone, 4-hydroxy-4'-fluorobenzophenone; 4,2'-dihydroxy-benzophenone; 4,2',4'-trihydroxy-3,5-dimethyl-benzophenone; 4,2',4'-trihydroxy-benzophenone; 2,4-dihydroxybenzophenone; 4-hydroxy-4'-methoxy-benzophenone; 4,4'-dihydroxy-2,6-dimethyl-benzophenone; 4-hydroxy-4'-(4-hydroxybenzoyl)-diphenyl; 1,4-bis(4-hydroxybenzoyl)-benzene; and 1,3-bis(4-hydroxybenzoyl)-benzene.

If high yields of hydroxy arylophenone are to be obtained in the process of the present invention, it is preferable to employ substantially stoichiometric proportions of the aromatic carboxylic acid $Ar(-CO_2H)_p$ and aromatic compound H—Ar'—OH. Thus if x moles of $Ar(-CO_2H)_p$ are used then preferably substantially xp moles of H—Ar'—OH should be employed. In the case where p is 1 it is thus preferably to employ substantially equimolar proportions of the aromatic carboxylic acid Ar—$CO_2H$ and the aromatic compound H—Ar'—OH. A small molar excess of H—Ar'—OH, e.g. up to a 15% molar excess, over the stoichiometric quantity of aromatic carboxylic acid may be advantageous in some cases.

The amount of alkane sulphonic acid to use should normally be such that there are at least 5 moles of alkane sulphonic acid per mole of aromatic carboxylic acid (e.g. 5-20 moles alkane sulphonic acid per mole of carboxylic acid); the alkane sulphonic acid then acts as an effective solvent and catalyst for the reaction. However, in some cases it may be more cost effective to employ a smaller quantity of the alkane sulphonic acid (e.g. 0.5-3 moles of alkane sulphonic acid per mole of carboxylic acid) because although a relatively small yield of hydroxy arylophenone will probably ensue, a production plant using such a process might be more economic in view of the usage of smaller quantities of the alkane sulphonic acid (which is expensive and would almost certainly be recycled in a commercial operation).

The process of the present invention may advantageously incorporate an azeotrope-forming liquid which is preferably a non-solvent for the reaction product. Suitable examples include aliphatic organic liquids such as hexane and cyclohexane. The water formed from the condensation may thus be removed by heating at reflux and removing the azeotrope that is formed by azeotropic distillation.

The process of the invention is best carried out at an elevated temperature, e.g. at at least 50° C., and a preferred range to employ is 50° C. to the reflux temperature of the reaction mixture. The optimum reaction temperature (or temperature range) should be determined by experiment for any particular reaction. The mixture from the reaction may be conveniently be worked up by pouring into water, and separating, washing and drying the hydroxy arylophenone product (recrystallizing if necessary).

It is fairly certain that the process of the present invention proceeds via the ester intermediate (H—Ar'—O—CO—)$_p$Ar which then rearranges, presumably through a Fries-type mechanism, to form the hydroxy arylophenone $Ar(-CO-Ar'-OH)_p$. The evidence for this is as follows.

Firstly it has been found that the ester intermediate can be isolated in a typical reaction (exemplified by the use of the reactants phenol and 4-hydroxy benzoic acid) using an excess of the phenol to encourage ester formation, examination of the product by thin layer chromatography (tlc) showing the presence of a small amount of the hydroxy arylophenone in addition to a major proportion of the ester. In reactions where the ester has not been isolated (when using substantially stoichiometric proportions of carboxylic acid and hydroxy aromatic compound) periodic sampling has been carried out in many cases and examination of the samples by tlc has shown that the reactions are proceeding through the ester intermediates.

Secondly, starting from the ester (H—Ar'—O—CO—)$_p$Ar it is possible to prepare the hydroxy arylophenone $Ar(-CO-Ar'-OH)_p$ in high yield and purity by reaction in the presence of an alkane sulphonic acid, particularly methane sulphonic acid.

The formation of the ester intermediates may be effected by reacting an aromatic carboxylic acid of formula $Ar(-CO_2H)_p$ with an aromatic compound of formula H—Ar'—OH in the presence of an alkane sulphonic acid to produce an ester of formula (H—Ar'—O—CO—)$_p$Ar. The structures of the aromatic carboxylic acid and hydroxy aromatic compound are as defined hereinbefore and it is particularly preferable to employ methane sulphonic acid.

The reaction conditions or procedure should of course be such as to enable the ester (rather than the hydroxy arylophenone) to be isolated in good yield, e.g. by appropriate adjustment of the stoichiometric proportions of the reactants (e.g. using a substantial molar excess of hydroxy aromatic compound over carboxylic acid such as 2 to 4 moles of aromatic compound per mole of carboxylic acid in the case where p is 1), by the use of a lower reaction temperature (e.g. ambient temperature), by the use of much smaller quantities of alkane sulphonic acid (e.g. the use of 5-20 moles of carboxylic acid per mole of alkane sulphonic acid), or by the termination of the reaction after a suitable period of time (these conditions should be determined by experiment for any particular reaction). In most respects, however, the reaction conditions will of course be similar to those employed for the preparation of the hydroxy arylophenone (including the use of an azeotrope-forming liquid and product work-up).

The reaction to form the hydroxy arylophenone which starts from ester is also a valuable discovery as it may enable the hydroxy arylophenone to be prepared in a much purer form, and it may therefore be advantageous to employ this process (i.e. starting from the ester itself) to prepare the hydroxy arylophenone of the invention.

Accordingly, there is also provided according to the invention a process for the production of a hydroxy arylophenone which comprises reacting an aryl ester of an aromatic carboxylic acid having the formula (H—Ar'—O—CO—)$_p$Ar where Ar is an aromatic radical to which the carbonyl group of the ester linkage is aromatically bound, Ar' is an aromatic radical containing at least one benzenoid ring with the hydrogen atom —H and the oxygen atom of the ester linkage —O— being aromatically bound para to each other in a benzenoid ring, and p is an integer of 1 or 2, in the presence of an alkane sulphonic acid to produce a hydroxy arylophenone of formula Ar(—CO—Ar'—OH)$_p$ where the carbonyl group is para to the hydroxyl group in said ester oxygen-containing benzenoid ring of Ar'.

A notable feature of this ester rearrangement is that it proceeds primarily to yield the para rather than the ortho product, since it is the para product which is obtained in high yield.

The aromatic radicals Ar and Ar' of the ester may be nuclear unsubstituted (apart from the carbonyl group of the ester linkage on Ar and the ester oxygen linkage on Ar') or have one or more nuclear substituents provided that the substituent(s) does not deleteriously affect the reaction to hydroxy arylophenone. Preferably the aryl ester has only one ester linkage, i.e. p is 1, and preferred esters that may be used have the formula

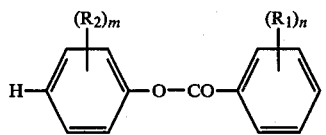

where n, m, R$_1$ and R$_2$ are as defined hereinbefore. Preferably n is 0, 1, 2 or 3; R$_1$ is hydroxyl, alkyl (1 to 5 carbon atoms), alkoxy (1 to 5 carbon atoms), F, Cl or (when n=1) a benzenoid ring fused to the benzene ring; m is 0, 1, or 2; and R$_2$ is alkyl (1 to 5 carbon atoms), alkoxy (1 to 5 carbon atoms), F, Cl, hydroxyl, or (when m=1) a benzenoid ring fused to the benzene ring.

Illustrative examples of esters which may be used are phenyl benzoate; phenyl-4-hydroxybenzoate; phenyl-2-hydroxybenzoate; phenyl-4-chlorobenzoate; phenyl-4-fluorobenzoate; 2,6-dimethylphenyl-2,4-dihydroxybenzoate; phenyl-2,4-dihydroxybenzoate; 3-hydroxyphenyl benzoate; phenyl-4-methoxybenzoate; 3,5-dimethoxyphenyl-4-hydroxybenzoate; and di-(4-hydroxyphenyl)-terephthalate. These esters yield according to the invention 4-hydroxy-benzophenone; 4,4'-dihydroxy-benzophenone; 4,2'-dihydroxy-benzophenone; 4-hydroxy-4'-chloro-benzophenone; 4-hydroxy-4'-fluorobenzophenone; 4,2',4'-trihydroxy-3,5-dimethylbenzophenone, 4,2',4'-trihydroxy-benzophenone; 2,4-dihydroxy-benzophenone; 4-hydroxy-4'-methoxy-benzophenone; 4,4'-dihydroxy-2,6-dimethyl-benzophenone; and 1,4-bis(4-hydroxybenzoyl)-benzene respectively.

In most respects, the reaction conditions will be similar to those employed for the preparations of hydroxy arylophenones starting from aromatic carboxylic acid and phenolic compound (including reaction temperature and product work up), although of course an azeotrope-forming liquid is not required as an option (provided water is not initially present). Again, the preferred alkane sulphonic acid to employ is methane sulphonic acid.

The present invention is now illustrated by the following examples.

EXAMPLE 1

4-Hydroxy benzoic acid (13.8 g; 0.10 mole), phenol (10.3 g; 0.11 mole), and 98% methane sulphonic acid (50 ml; 75.5 g; 0.8 mole) were mixed and warmed to 80° C. The yellow solution formed was maintained at this temperature for 4.5 hours. During this period small samples were taken periodically and examined by tlc; this showed the formation and subsequent almost complete disappearance of phenyl-4-hydroxybenzoate and the progressively increasing formation of 4,4'-dihydroxy-benzophenone (using comparisons with authentic samples). The yellow solution was poured into hot water (500 ml) and cooled with stirring to yield a crystalline product. The crystalline product was collected, washed with water and dried at 110° C. in a vacuum oven. The yield of product, 4,4'-dihydroxy-benzophenone (identified by comparison of infra-red spectrum with an authentic specimen) was 11.0 g (51%).

EXAMPLE 2

4-Hydroxy benzoic acid (13.8 g; 0.10 mole), phenol (10.3 g; 0.11 mole), 98% methane sulphonic acid (50 ml; 75.5 g; 0.8 mole) and cyclohexane (10 ml) were mixed and heated to reflux temperature. The solution was refluxed for 12 hours using a Dean and Stark apparatus (no sampling). The reaction mixture was worked up to give 4,4'-dihydroxy-benzophenone in 70% yield.

EXAMPLE 3

Example 2 was repeated except that the quantities of reactants employed were as follows: 4-hydroxy benzoic acid (138 g; 1 mole), phenol (100 g; 1.1 mole), methane sulphonic acid (96 g; 1 mole), and cyclohexane (100 ml). The yield of 4,4'-dihydroxy-benzophenone was 20%.

EXAMPLE 4

Phenyl-4-hydroxybenzoate (5.0 g; 0.02 mole) was heated with 98% methane sulphonic acid (10 ml; 15.1 g; 0.16 mole) at 80° C. for 2 hours. The solution was poured into water and the solid product washed with water and dried at 110° C. in a vacuum oven to yield 4,4'-dihydroxy-benzophenone (infra-red spectrum indentical with that of an authentic sample); the yield was 3.4 g (68%).

EXAMPLE 5

Phenyl benzoate (5.0 g; 0.025 mole) was heated with 98% methane sulphonic acid (15 ml; 22.65 g; 0.24 mole) at 100° C. for 2 hours. The resulting solution was poured into ice water whereby a crystalline product separated out. Analysis by tlc showed this to be 4-hydroxy-benzophenone; the yield was 3.5 g (70%).

Recrystallisation from a mixture of ethanol (15 ml) and water (15 ml) gave pure 4-hydroxy-benzophenone of melting point 133° C. (literature 135° C.) whose infrared spectrum was identical to that of an authentic sample.

EXAMPLE 6 (COMPARATIVE)

4-Hydroxy-benzoic acid (13.8 g; 0.10 mole), and phenol (28.2 g; 0.30 mole), were heated to 200° C. to form a homogenous solution. 98% Methane sulphonic acid (0.5 ml; 0.755 g; 0.008 mole) was added. The solution became yellow, began to boil and some water distilled off. After 30 minutes reaction the orange yellow mixture was poured into cold water (100 ml) and stirred to yield a solid. This was washed repeatedly (100 ml×3) with cold water, and then dried at 70° C. in a vacuum oven. The product had melting point 170°–177° C. Analysis by tlc showed it to be primarily phenyl-4-hydroxybenzoate with a trace of 4,4'-dihydroxy-benzophenone being present; the infra-red and nuclear magnetic resonance spectra also showed the product to be phenyl-4-hydroxybenzoate. The yield was 13.9 g (65%).

I claim:

1. A process for the production of a hydroxy arylophenone which comprises reacting substantially stoichiometric proportions of (i) an aromatic carboxylic acid of formula AR(—CO$_2$H)$_p$ where Ar is an aromatic radical, (—CO$_2$H) is an aromatically bound carboxylic acid group, and p is an integer of 1 or 2, with (ii) an aromatic compound of formula

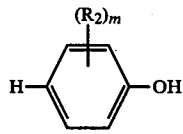

where m is 0, 1, or 2, and R$_2$ which may be the same or when (m=2) different represents alkyl (1 to 5 carbon atoms), alkoxy (1 to 5 carbon atoms), F, Cl, or a benzene ring fused to the hydroxyl-substituted benzene ring to form a naphthalene nucleus therewith, in the presence of an alkane sulphonic acid and at a reaction temperature of at least 50° C. to produce a para hydroxy arylophenone of the formula

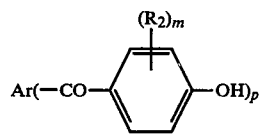

2. A process according to claim 1 wherein the alkane sulphonic acid used is methane sulphonic acid.

3. A process according to claim 1 wherein the integer p of the aromatic carboxylic acid used is 1.

4. A process according to claim 1 wherein the aromatic carboxylic acid has the formula

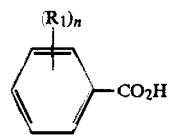

where n is 0, 1, 2, or 3, and R$_1$ which may be the same or (where n=2) different represents alkyl (1 to 5 carbon atoms), alkoxy (1 to 5 carbon atoms), hydroxyl, F, Cl or a benzene ring fused to the carboxyl-substituted benzene ring to form a naphthalene nucleus therewith.

5. A process according to claim 1 wherein at least 5 moles of alkane sulphonic acid per mole of aromatic carboxylic acid are used.

6. A process according to claim 1 wherein 0.5–3 moles of alkane sulphonic acid per mole of aromatic carboxylic acid are used.

7. A process according to claim 1 wherein an azeotrope-forming liquid which is a non-solvent for the reaction product is employed and the water formed from the reaction is removed by azeotropic distillation.

8. A process according to claim 1 wherein the reaction temperature is within the range 50° C. to the reflux temperature of the reaction mixture.

9. A process for the production of a hydroxyl arylophenone which comprises reacting an aryl ester of an aromatic carboxylic acid having the formula

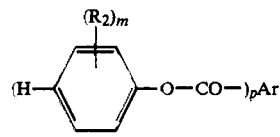

where Ar is an aromatic radical to which the carbonyl group of the ester linkage is aromatically bound and p is an integer of 1 or 2, and where m is 0, 1, or 2, and R$_2$ which may be the same or (when m=2) different represents alkyl (1 to 5 carbon atoms), alkoxy (1 to 5 carbon atoms), F, Cl, or a benzene ring fused to the oxo-substituted benzene ring to form a naphthalene nucleus therewith, in the presence of an alkane sulphonic acid and at a reaction temperature of at least 50° C. to produce a para hydroxy arylophenone of formula

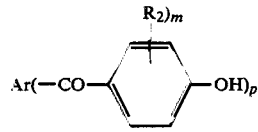

10. A process according to claim 9 wherein the alkane sulphonic acid used is methane sulphonic acid.

11. A process according to claim 9 wherein the integer p of the aryl ester is 1.

12. A process according to claim 9 wherein the aryl ester used has the formula

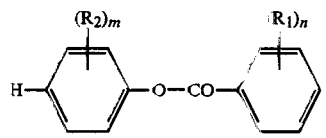

where n is 0, 1, 2, or 3, and $R_1$ which may be the same or (when n=2) different represents alkyl (1 to 5 carbon atoms), alkoxy (1 to 5 carbon atoms), hydroxyl, F, Cl or a benzene ring fused to the carbonyl-substituted benzene ring to form a naphthalene nucleus therewith.

13. A process according to claim 9 wherein at least 5 moles of alkane sulphonic acid per mole of aryl ester are employed.

14. A process according to claim 9 wherein 0.5–3 moles of alkane sulphonic acid per mole of aryl ester are employed.

15. A process according to claim 9 wherein the reaction temperature is within the range 50° C. to the reflux temperature of the reaction mixture.

* * * * *